United States Patent
Chodkowski et al.

(10) Patent No.: US 10,080,858 B2
(45) Date of Patent: Sep. 25, 2018

(54) COLLAPSIBLE PATIENT CONDUIT A RESPIRATORY THERAPY SYSTEM

(71) Applicant: KONINKLIJKE PHILIPS N.V., Eindhoven (NL)

(72) Inventors: Lauren Patricia Chodkowski, Pittsburgh, PA (US); Jerome Matula, Jr., Apollo, PA (US); Dina Colangelo, Murrysville, PA (US); Michael Joseph Zadrozny, Coatesville, PA (US); Alicia Marie Brentzel, Jeannette, PA (US); Adam Michael Neff, Oakmont, PA (US); Richard Thomas Haibach, Verona, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 204 days.

(21) Appl. No.: 14/353,809

(22) PCT Filed: Oct. 5, 2012

(86) PCT No.: PCT/IB2012/055366
§ 371 (c)(1),
(2) Date: Apr. 24, 2014

(87) PCT Pub. No.: WO2013/061187
PCT Pub. Date: May 2, 2013

(65) Prior Publication Data
US 2014/0299131 A1 Oct. 9, 2014

Related U.S. Application Data

(60) Provisional application No. 61/551,973, filed on Oct. 27, 2011.

(51) Int. Cl.
*A61M 16/08* (2006.01)

(52) U.S. Cl.
CPC . *A61M 16/0875* (2013.01); *A61M 2205/0216* (2013.01); *A61M 2205/0266* (2013.01); *A61M 2209/06* (2013.01)

(58) Field of Classification Search
CPC .......... A61M 16/0875; A61M 2209/06; A61M 2205/0266; A61M 2205/0216; F16L 11/02; F16L 11/08; F16L 11/082; F16L 11/112
See application file for complete search history.

(56) References Cited

U.S. PATENT DOCUMENTS 3,581,778 A * 6/1971 Korejwa ................ B29C 47/02
138/119
3,861,424 A 1/1975 Mizutani
(Continued)

FOREIGN PATENT DOCUMENTS

CN 102458549 A 5/2012
EP 1820528 A1 8/2007
(Continued)

OTHER PUBLICATIONS

Stockel, Dieter, "The Shape Memory Effect", 2000.*
How it Works—Developing a Good Memory: Nitinol Shape Memory Allow, Jan. 3, 2010, Today's Machining World.*

*Primary Examiner* — Gregory Anderson
*Assistant Examiner* — Margaret Luarca
(74) *Attorney, Agent, or Firm* — Michael W. Haas

(57) ABSTRACT

An elongated flexible conduit (4) includes an flow element (24) having a first elongated wall segment (32) and a second elongated wall segment (44) that are connected together at their sides to form a wall (28) that is continuous in a circumferential direction perpendicular to the direction of elongation (8). The flow element is movable between a first configuration and a second configuration (68), with the first configuration being an expanded configuration, and with the
(Continued)

second configuration being a collapsed configuration. The flow element can be moved from its expanded configuration to its collapsed configuration, such as for purposes of packing during traveling, and can then be moved from its collapsed configuration back to its expanded configuration in any of a variety of fashions in order to return the flow element to a condition in which it can carry a flow of breathing gas from a CPAP machine (12) to a CPAP mask (16).

11 Claims, 3 Drawing Sheets

(56) References Cited

U.S. PATENT DOCUMENTS

| | | | | |
|---|---|---|---|---|
| 4,302,266 | A * | 11/1981 | Kutnyak | B29C 47/0023 |
| | | | | 156/149 |
| 4,986,951 | A * | 1/1991 | Ledoux | B29C 63/343 |
| | | | | 138/97 |
| 5,165,417 | A | 11/1992 | Murphy, Jr. | |
| 5,167,164 | A | 12/1992 | Maekawa | |
| 5,454,061 | A | 9/1995 | Carlson | |
| 5,711,296 | A * | 1/1998 | Kolobow | A61M 16/00 |
| | | | | 128/204.28 |
| 6,183,493 | B1 | 2/2001 | Zammit | |
| 2004/0237192 | A1 * | 12/2004 | Holub | A47G 9/086 |
| | | | | 5/413 R |
| 2005/0202194 | A1 * | 9/2005 | Browne | F16K 7/02 |
| | | | | 428/36.9 |
| 2006/0113690 | A1 | 6/2006 | Huddart et al. | |
| 2007/0208300 | A1 * | 9/2007 | Pravong | A61M 1/008 |
| | | | | 604/96.01 |
| 2007/0215156 | A1 | 9/2007 | Kwok | |
| 2008/0173305 | A1 | 7/2008 | Frater | |
| 2009/0266365 | A1 | 10/2009 | Oberle | |
| 2010/0036307 | A1 * | 2/2010 | Von Segesser | A61B 17/3439 |
| | | | | 604/6.16 |
| 2010/0236552 | A1 * | 9/2010 | Kwok | A61M 16/0057 |
| | | | | 128/204.21 |

FOREIGN PATENT DOCUMENTS

| | | |
|---|---|---|
| JP | H0531679 A | 2/1993 |
| JP | 2009511173 A | 3/2009 |
| JP | 2011125628 A | 6/2011 |
| WO | 03028614 A2 | 4/2003 |
| WO | 2004020031 A1 | 3/2004 |
| WO | WO2005099801 A1 | 10/2005 |
| WO | 2006130322 A2 | 12/2006 |
| WO | WO2007019624 A1 | 2/2007 |
| WO | WO2007047151 A1 | 4/2007 |
| WO | WO2007109837 A1 | 10/2007 |
| WO | WO2008011682 A1 | 1/2008 |
| WO | WO2008021201 A1 | 2/2008 |
| WO | WO2010091462 A1 | 8/2010 |

* cited by examiner

COLLAPSIBLE PATIENT CONDUIT A RESPIRATORY THERAPY SYSTEM

CROSS-REFERENCE TO RELATED APPLICATIONS

This patent application claims the priority benefit under 35 U.S.C. § 371 of international patent application no. PCT/IB2012/055366, filed Oct. 5, 2012, which claims the priority benefit under 35 U.S.C. § 119(e) of U.S. Provisional Application No. 61/551,973 filed on Oct. 27, 2011, the contents of which are herein incorporated by reference.

BACKGROUND OF THE INVENTION

1. Field of the Invention

The present invention pertains to a conduit for delivering a flow of breathing gas to a patient and, in particular, to an improved conduit that is movable between and expanded configuration and a collapsed configuration.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a respiratory patient interface device including a mask apparatus that is typically secured on the face of a patient by a headgear assembly. The mask apparatus may be, without limitation, a nasal mask that covers the patient's nose, a nasal cushion having nasal prongs that are received within the patient's nares, a nasal/oral mask that covers the nose and mouth, or full face mask that covers the patient's face. It is known to maintain such devices on the face of a wearer by a headgear having one or more straps adapted to fit over/around the patient's head. Because such respiratory patient interface devices are typically worn for an extended period of time, it is important for the headgear to maintain the mask apparatus in a desired position while doing so in a manner that is comfortable to the patient.

While such systems have been generally effective for their intended purposes, they have not been without limitation. For example, when a patient is travelling they typically will pack (such as in a suitcase, etc.) a system that may include a CPAP machine, a CPAP mask, and a flexible conduit that connects between the CPAP machine and the CPAP mask to provide a flow of breathing gas from the CPAP machine to the CPAP mask and to the airways of the patient. Such components can have unusual shapes and/or can be cumbersome to pack. It thus would be desirable to provide a solution to help overcome such shortcomings and other limitations known in the relevant art.

SUMMARY OF THE INVENTION

In certain embodiments, the general nature of the invention can be stated as including an elongated flexible conduit that is structured to extend between a source of breathing gas and a patient interface. The conduit is structured to communicate a flow of breathing gas between the source of breathing gas and the patient interface to provide the flow of breathing gas to a patient. The conduit can be generally stated as including an elongated flow element comprising a first elongated wall segment and a second elongated wall segment. The first wall segment is connected longitudinally at its sides with the second wall segment to form as the elongated flow element a wall that is continuous in a circumferential direction perpendicular to the direction of elongation. The flow element is structured to be movable between a first configuration and a second configuration. The first configuration is an expanded configuration wherein the wall is of a nominally annular cross sectional shape wherein at least a portion of a first inner surface of the first wall segment and at least a portion of a second inner surface of the second wall segment are opposed to one another and extend about a perimeter of an elongated interior region that is structured to carry the flow of breathing gas. The second configuration is a collapsed configuration wherein at least a portion of the first surface and at least a portion of the second inner surface are engaged with one another.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
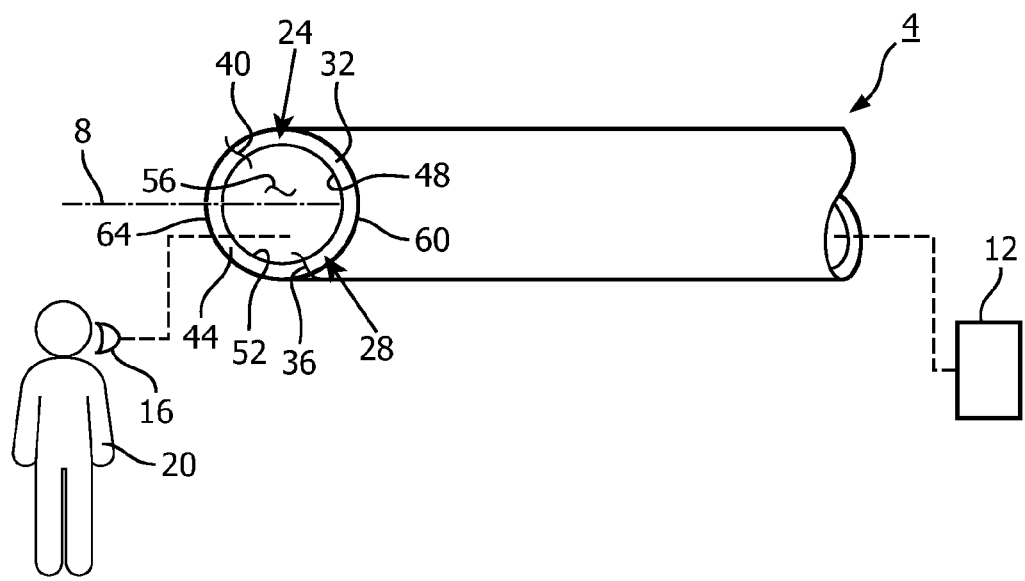
FIG. 1 is a front elevational view of an improved conduit in accordance with a first embodiment of the present invention in a first, expanded configuration and schematically depicted as being connected between a source of breathing gas and a patient interface to provide a flow of breathing gas to a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

An improved conduit 4 in accordance with a first embodiment of the present invention is depicted generally in FIG. 1. Conduit 4 is a flexible element that is elongated along a direction of elongation that is indicated generally at the numeral 8 in FIG. 1. Conduit 4 is configured to be connected between a source of breathing gas 12 and a patient interface 16, as is depicted schematically in FIG. 1. Source of breathing gas 12 may be any of a variety of devices such as a CPAP machine, etc., without limitation, that is configured to provide a flow of breathing gas. Conduit 4 is depicted in FIG. 1 as being in a first configuration, which is an expanded configuration, whereby it functions as a tube to communicate the flow of breathing gas between source of breathing gas 12 and patient interface 16. More particularly, by providing the flow of breathing gas to patient interface 16, the flow of breathing gas is provided to the airways of a patient 20. Conduit 4 thus enables source of breathing gas 12 to be in fluid communication with patient interface 16 and thus with the airways of patient 20.

When conduit 4 is in its expanded configuration, as is depicted generally in FIG. 1, conduit 4 provides an elongated flow element 24 that can generally be said to include a wall 28 that is of a nominally annular shape. That is to say that wall 28 has an annular shape in one of its configurations, notably the configuration that occurs during the course of its intended use, but that it is capable of other configurations such as will be set forth in greater detail below. It is also noted that the expression "annular" is not intended to be limited to shapes that are purely circular in nature but can also encompass shapes such as elliptical shapes, oval shapes, and the like without limitation. Stated otherwise, flow element 24 is of a hollow, arcuate cross-section in one of its configurations, but is of other cross-sectional shapes in other configurations, as will be described in greater detail below.

Wall 28 can be said to include a first segment 32 that extends between a first location 36 on wall 28 and a second location 40 on wall 28. Moreover, wall 28 can be said to further include a second segment 44 that extends between first and second locations 36 and 40. In this regard, it is expressly noted that first and second segments 36 and 44 are not intended to refer to specific portions of wall 28, but rather are intended to refer to any portions of wall 28 that can be said to extend between a pair of locations on wall 28. In this regard, therefore, first and second locations 36 and 40 are provided merely as exemplary locations on wall 28 between which a pair of segments can be said to exist. First and second locations 36 and 40 thus can refer to any two locations along wall 28 without limitation. Furthermore, first and second segments 32 and 44 thus can likewise be said to refer to any two segments of wall 28 that are situated between a common pair of points on wall 28. First and second segments 32 and 44 need not be situated in any particular orientation with respect to one another and need not be of equal size.

First and second segments 32 and 44 are both elongated and can be said to each have a pair of sides, with the sides of first segment 32 and the sides of second segment 44 being connected together such that they form wall 28. Wall 28 is continuous in a circumferential direction perpendicular to direction of elongation 8. That is, wall 28 can be generally said to be unbroken and without voids (within the range of operating pressures typically experienced by conduit 4) in a circumferential direction when going from first segment 32 to second segment 44 and likewise when further going from second segment 44 to first segment 32.

First segment 32 can be said to have a first inner surface 48, and second segment 44 can be said to have a second inner surface 52. First and second inner surfaces 48 and 52 are contiguous and can be said to extend about an interior 56 of flow element 24. In this regard, it is understood that the flow of breathing gas are carried through interior 56 between source of breathing gas 12 and patient interface 16. First segment 32 can further be said to have a first outer surface 60, and second segment 44 can likewise be said to have a second outer surface 64. First and second outer surfaces 60 and 64 are contiguous.

Figure 2:
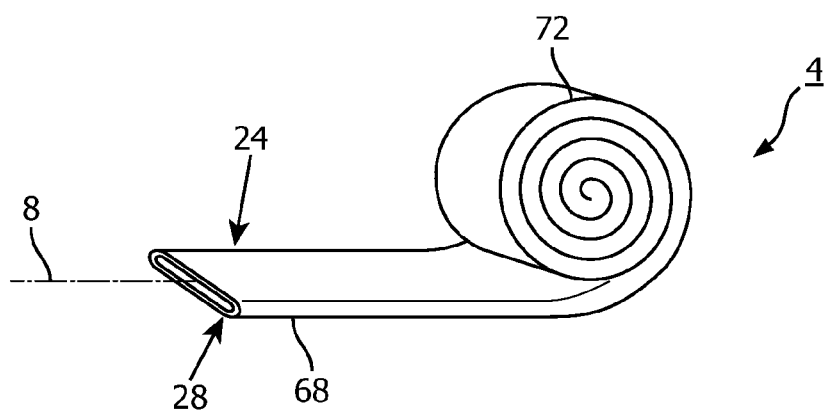
FIG. 2 is a front elevational view of the conduit of FIG. 1 partially in a second, collapsed configuration and partially in a third, rolled configuration.

As can be understood from FIG. 2, conduit 4 is movable from its expanded configuration of FIG. 1 to a second configuration which, in the exemplary embodiment depicted herein, is a collapsed configuration that is indicated generally at the numeral 68 in FIG. 2. In collapsed configuration 68, first and second inner surfaces 48 and 52 are engaged with one another whereby interior 56 essentially ceases to exist.

As can further be seen from FIG. 2, flow element 24 in its collapsed configuration can further be moved into a third configuration which, in the exemplary embodiment depicted herein, is a rolled configuration that is indicated generally at the numeral 72 in FIG. 2. It is noted that in alternative embodiments not expressly depicted herein, the third configuration could be any other type of reduced configuration, such as an accordion-style crunched configuration, etc., as will be apparent to one of ordinary skill in the art.

In rolled configuration 72, first outer surface 60 and second outer surface 64 are engaged with one another. Moreover, wall 28 is rolled about a rolling axis that is oriented substantially perpendicular to direction of elongation 8. While FIG. 2 depicts a portion of conduit 4 being in collapsed configuration 68 and the remaining portion being in rolled configuration 72, it is understood that FIG. 2 is intended to demonstrate how conduit 4 can be moved from expanded configuration 4 to collapsed configuration 68 to rolled configuration 72, and it is to be understood that the entire length of conduit 4 typically will be in rolled configuration 72 when conduit 4 is in a compact condition for, say, traveling or otherwise.

It is also noted that the example of rolled configuration 72 provided in FIG. 2 is not intended to be limiting. That is, it is to be understood that conduit 4 in the rolled configuration could be more loosely rolled such as in the form of a hoop with an open center rather than the disc configuration depicted generally in FIG. 2. Moreover, conduit 4 need not be repeatedly rolled about the axis perpendicular to direction of elongation 8, and rather it is understood that conduit 4 could instead, for example, be situated along the interior walls of a suitcase such as would enable conduit 4 to be engaged between an inner surface of the wall of the suitcase and clothing or other objects within the interior of such a suitcase, by way of example.

Conduit 4 could be formed of substantially any materials that enable it to move among its various configurations and communicate the flow of breathing gas between source of breathing gas 12 and patient interface 16. In its simplest example, conduit 4 may be formed of a flexible, collapsible material such as an elastomeric silicone or polyurethane material that is configured in the form of a collapsible hose. In other embodiments described in greater detail below, other materials may be employed. It is to be understood, however, that virtually any material or combination of materials can be employed to achieve the objectives of the present invention without limitation.

Figure 3:
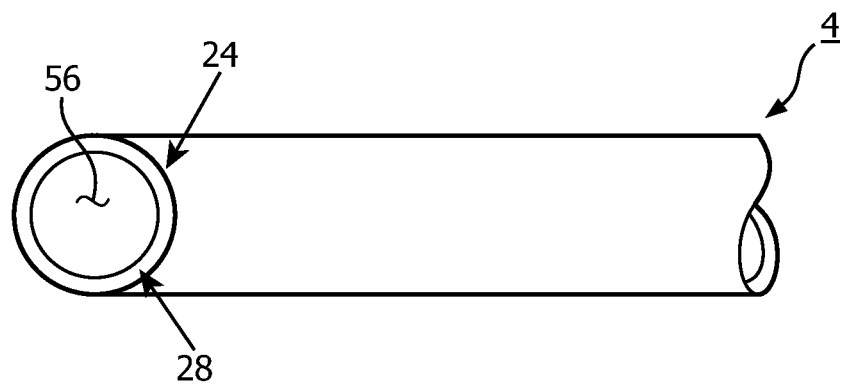
FIG. 3 is a view similar to FIG. 1, except depicting the conduit returned to the expanded configuration from either of the configurations depicted generally in FIG. 2.

FIG. 3 can be said to generally depict conduit 4 once it has been returned from its third or second configurations to its first configuration. In the exemplary embodiment depicted generally in FIGS. 1-3, conduit 4 has returned from its collapsed or rolled configurations 68 or 72 (as in FIG. 2) to its expanded configuration (as in FIGS. 1 and 3) based upon, for example, connecting conduit 4 with source of breathing gas 12 and applying an increased pressure to interior 56 of conduit 4. Such an increased pressure can result from providing a flow of breathing gas from source of breathing gas 12. Alternatively, and by way of example, conduit 4 can be returned to its expanded configuration by patient 20 blowing into interior 56 to provide an increased pressure within interior 56.

It thus can be seen that conduit 4 is movable among expanded, collapsed, and rolled configurations as depicted in FIGS. 1-3. Such variability of the configuration of conduit 4 enables conduit 4 to communicate a flow of breathing gas to patient 20 while also being convenient to store, pack, and move from one location to another. Such movement among the various configurations can be performed by manually collapsing, manually rolling, and manually expanding wall 28 as needed.

Figure 4:
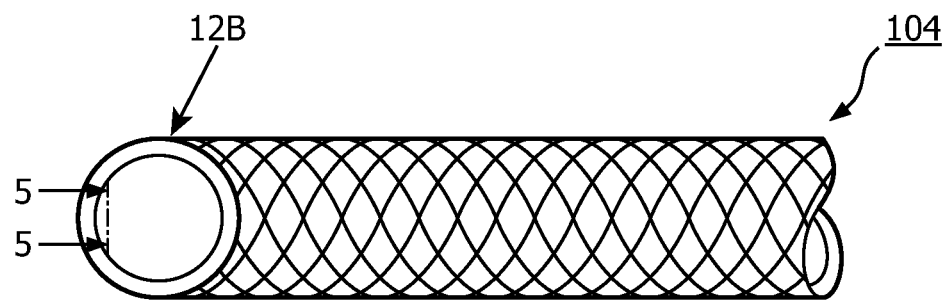
FIG. 4 is a front elevational view of an improved conduit in accordance with a second embodiment of the present invention.
Figure 5:
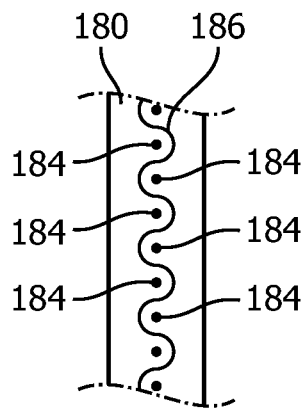
FIG. 5 is a sectional view as taken along line 5-5 of FIG. 4.

An improved conduit 104 in accordance with a second embodiment of the present invention is depicted generally in FIGS. 4 and 5. Conduit 104 can be said to be similar to conduit 4, except that conduit 104 is further defined as having a wall 128 of a specific reinforced structure. More particularly, wall 128 can be said to include a reinforcement element 176 and a casing 180, with casing 180 being in physical contact with and engaged with reinforcement element 176. By way of example, reinforcement element 176 may be configured to strengthen wall 128 against the pressure differential between the flow of breathing gas carried within the interior of conduit 104 and the exterior conduit 104.

Moreover, casing 180 can be said to provide a seal that is sufficiently airtight to carry the flow of breathing gas between source of breathing gas 12 and patient interface such that the flow of breathing gas is delivered to the airways of patient 20. As such, casing 180 can be of many forms such as a separate coating on the interior surface or the exterior surface of reinforcement element 176, or it could be a layer within which reinforcement element 176 is embedded, by way of example. By way of further example, casing 180 potentially could be formed by applying a coating or other treatment to the structures that form reinforcement element 176, with such structures and such coating then undergoing some type of material change during manufacture. As an example, the materials that make up reinforcement element 176 could be coated with a resinous material which, in the presence of heat, could be caused to form a contiguous plastic coating that is of sufficient density that it can seal the flow of breathing gas within the interior of wall 128 during use of conduit 104. Other examples of casing 180 will be apparent of one of ordinary skill in the art.

Reinforcement element 176 can be configured in any of a variety of fashions. In the exemplary embodiment depicted in FIGS. 4 and 5, reinforcement element 176 is a woven structure. FIG. 5 depicts in a schematic fashion that reinforcement element 176 includes a plurality of warp fibers 184 and weft fibers 186 (also known as woof fibers) that are woven together. It is emphasized, however, that warp and weft fibers 184 and 186 are intended to schematically depict that reinforcement element 176 has a woven characteristic, and it is understood that in other embodiments the woven characteristic could be of a knitted format, a mat format (such as might result from a plurality of fibers in various orientations that are pressed into a sheet, such as in the way a sheet of paper is formed from wood pulp) or other configurations.

In the exemplary embodiment depicted generally in FIGS. 4 and 5, conduit 104 is movable between an expanded configuration, such as is depicted generally in FIG. 4, and a collapsed configuration and/or a rolled configuration such as are demonstrated generally in FIG. 2 in connection with conduit 4. Such collapsing and/or rolling can be done manually, by way of example.

Conduit 104 can be returned from such a rolled and/or collapsed configuration to the expanded configuration (such as is depicted generally in FIG. 4) due, for example, to the natural elastic properties of conduit 104. For instance, the material out of which casing 180 is manufactured can be of a resilient nature which causes conduit 104 to automatically spring back to its expanded configuration from the collapsed and/or rolled configurations. In this regard, it may be desirable to maintain conduit 104 in its rolled configuration with the use of a strap, an elastic band, etc. which, once removed, will release conduit 104 and permit it to spring back to its expanded configuration.

It is also noted that such elastic expansion of conduit 104 can result, at least in part, from the properties possessed by the material out of which warp and weft fibers 184 and 186 are formed. For instance, aramid fibers and carbon fibers have a certain elastic characteristic which can cause them to spring back to an original condition once a load has been removed therefrom.

Virtually any type of fiber can be employed in such a fashion. For example, the warp fibers 184 and weft fibers 186 can be formed of a material that is metallic or partially metallic, such as a metal or a ceramic, or may be formed of a combination of such materials. For example, such a combination of metals may be beryllium and copper. In this regard, it is noted that warp fibers 184 and weft fibers 186 need not even be formed of the same materials or be arranged in any particular fashion. That is, warp fibers 184 and weft fibers 186 were provided merely as an example to demonstrate that reinforcement element 176 is woven in one fashion or another, meaning that the various fibers of reinforcement element 176 interact with one another and/or with themselves in some fashion. It is noted, however, that the various fibers that make up reinforcement element 176 could also possess specific properties and/or be oriented at specific angles with respect to one another in order to provide particular deformation characteristics, such as in the fashion of a fiber layup.

The fibers that form reinforcement element 176 additionally or alternatively can include fibers that are formed in whole or in part of a synthetic polymeric material, and/or can be formed in whole or in part of natural materials, by way of example. Likewise, casing 180 can be of any of a variety of materials without departing from the present concept. In this regard, it is expressly noted that in alternative embodiments conduit 104 can potentially be formed without casing 180 if reinforcement element 176 is woven with sufficient density that it can reliably communicate the flow of breathing gas between source of breathing gas 12 and patient interface 16. Other combinations will be apparent to those of ordinary skill in the art.

It is also expressly noted that conduit 104 need not be configured to elastically spring back to its expanded configuration from its collapsed or rolled configurations. Rather, the elastic return to its expanded configuration was merely provided as another example of the fashion in which conduit 104 or conduit 4 can be returned from their collapsed or rolled configurations to their expanded configurations. That is, either or both of conduits 4 and 104 can be configured to return to their expanded configurations either elastically, by application of a relatively greater pressure to the interior of conduit 4 or 104, or by another mechanism, without limitation.

Figure 6:
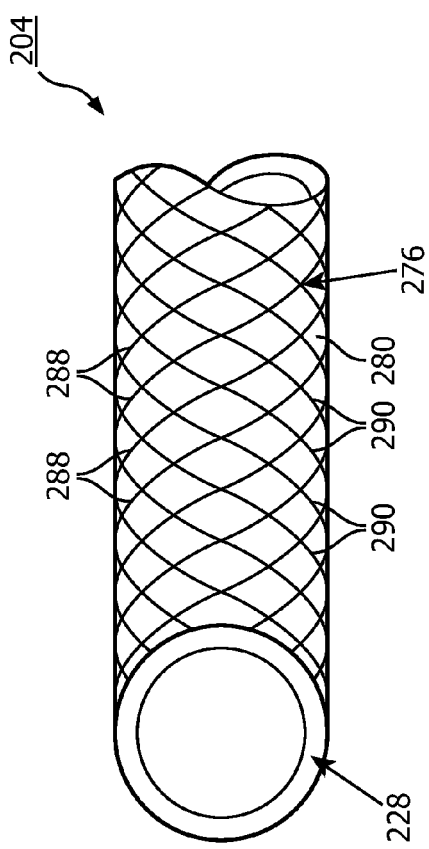
FIG. 6 is a front elevational view of an improved conduit in accordance with a third embodiment of the present invention.
Figure 7:
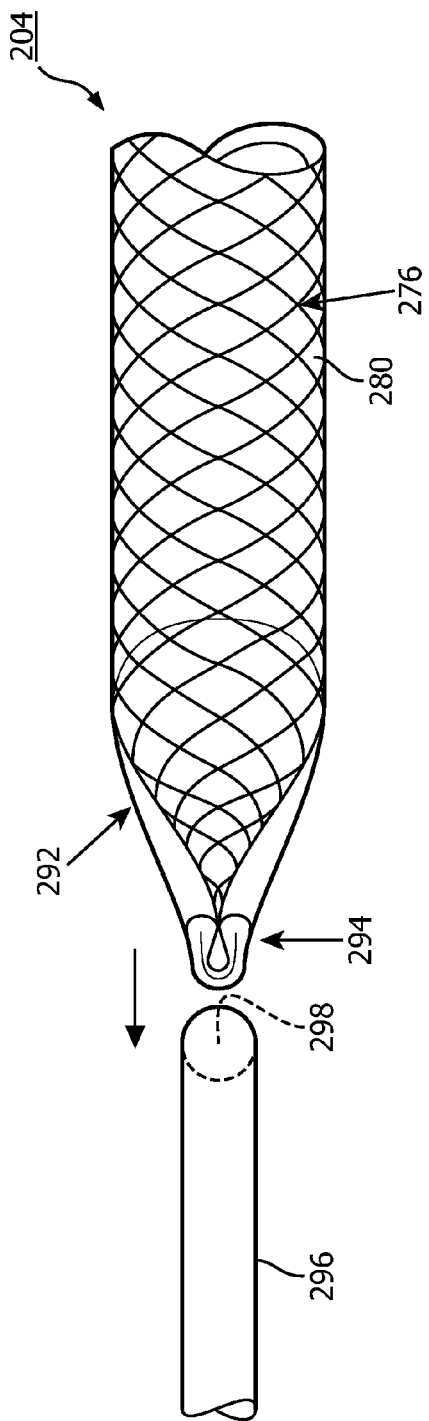
FIG. 7 is a front elevational view of the conduit of FIG. 7, at least a portion of which is in a second, collapsed configuration, and at least a portion of which is in a third, rolled configuration and being received in a sheath.

An improved conduit 204 in accordance with a third embodiment of the present invention is indicated generally in FIGS. 6 and 7. Conduit 204 includes a wall 228 that is formed of a reinforcement element 276 and a casing 280 in physical contact with one another. However, reinforcement element 276 of the exemplary conduit 204 is not necessarily woven and is of an overlaid configuration. That is, reinforcement element 276 includes a plurality of first fibers 288 oriented in a first direction and a plurality of second fibers 290 oriented in a second direction, with first fibers 288 overlying second fibers 290 or vice-versa. Alternatively, reinforcement element 276 in other embodiments potentially can include only one of first fibers 288 and second fibers 290. Depending upon the arrangement of such a single set of fibers, reinforcement element 276 potentially could be of an overlaid configuration or not, meaning that the set of fibers may be arranged to overlie itself via wrapping or other arrangement, or can simply be configured to be floating in relation to casing 280.

In the exemplary embodiment depicted generally in FIGS. 6 and 7, first and second fibers 288 and 290 are formed of a material having a shape memory. For example, the material may be of a cold-forged shape and may thereafter may be deformed from the cold-forged shape. However, depending upon a particular interaction with the material, the material can return to its original cold-forged shape. An example of such a material includes Nitinol, which is a nickel-titanium alloy, although other shape memory materials can be employed. For example, alloys of copper, zinc, aluminum, and nickel can be employed, as well as alloys of copper, aluminum, and nickel, and other alloys and materials.

By configuring reinforcement element 276 to include fibers having a shape memory, conduit 204 can be deformed in a desired fashion, such as by deforming conduit 204 from its expanded configuration of FIG. 6 to a collapsed or other configuration, and can then be returned to its original expanded configuration under a predetermined condition. In the example of Nitinol, the materials return to their original configuration with the application of a moderate amount of heat, such as can be provided by an electric hair dryer or through the application of hot water from a sink or shower. Other sources of heat will be apparent to those of ordinary skill in the art.

An example of the collapsing of conduit 204 is depicted generally in FIG. 7. Specifically, FIG. 7 depicts a portion of conduit 204 as being in a collapsed configuration as is indicated generally at the numeral 292 and which is exemplified by a flattened configuration of conduit 204. Moreover, a portion of conduit 204 is folded and/or rolled in a direction generally parallel with the direction of elongation of conduit 204, as is indicated generally at the numeral 294 in FIG. 7. Conduit 204 in its folded configuration 294 (which may include some rolling as suggested above) is receivable within a sheath 296 having a receptacle 298.

Sheath 296 maintains wall 228 in its folded and/or rolled configuration 294 within receptacle 298 for purposes of packing, travel, and the like. Conduit 204 can then be removed from sheath 296, after which it may remain in its folded and/or rolled configuration 294. If it is desired to return conduit 204 to its expanded configuration, the application of heat such as mentioned above will cause the shape memory feature of the Nitinol or other shape memory fibers of reinforcement element 276 to return to their cold-forged shape which corresponds with the expanded configuration of conduit 204. In this regard, it is expressly noted that the entirety of the fibers of reinforcement element 276 need not be formed of fibers having a shape memory, and it is rather understood that shape memory fibers in combination with other fibers or materials can be employed to form reinforcement element 276 depending upon the needs of the configuration.

It is also expressly noted that conduit 204 in its folded and/or rolled configuration 294 need not necessarily be returned to is expanded configuration through the application of heat or other predetermined condition. That is, reinforcement element 276 and/or casing 280 can be configured to cause wall 228 to elastically spring back to its expanded configuration from folded configuration 294. This can be accomplished by configuring sheath 296 such that it does not plastically deform, i.e., so that it does not inelastically deform, first and/or second fibers 288 and 290, whereby the elastic properties of first and second fibers 288 and 290 (potentially in combination with the elastic properties of casing 280) can cause conduit 204 to automatically elastically spring back to its expanded configuration. Other variations will be apparent to one of ordinary skill in the art.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An elongated flexible conduit structured to extend between a source of breathing gas and a patient interface, the conduit being structured to communicate a flow of breathing gas between the source of breathing gas and the patient interface to provide the flow of breathing gas to a patient, the conduit comprising:
   an elongated flow element, comprising a first elongated wall segment and a second elongated wall segment;
   the first wall segment being connected longitudinally with the second wall segment to form as the elongated flow element a wall that is continuous in a circumferential direction perpendicular to a direction of elongation;
   the flow element being structured to be movable between a first configuration and a second configuration;
   the first configuration being an expanded configuration wherein the wall is of a nominally annular cross sectional shape wherein at least a portion of a first inner surface of the first wall segment and at least a portion of a second inner surface of the second wall segment are opposed to one another and extend about a perimeter of an elongated interior region that is structured to carry the flow of breathing gas; and the second configuration being a collapsed configuration wherein at least a portion of the first surface and at least a portion of the second inner surface are engaged with one another; and
   the flow element being formed at least at least in part of a shape memory material which, in response to an application of an amount of heat to the flow element, is structured to return to a cold forged shape and to thereby return the wall from the collapsed configuration to the expanded configuration.

2. The conduit of claim 1, wherein the wall comprises a reinforcement element formed of fibers comprising at least one of:
   fibers formed of an at least partially metallic material;
   fibers formed of an at least partially synthetic polymeric material; and
   fibers formed of an at least partially natural material.

3. The conduit of claim 2, wherein the fibers comprise at least two of:
   fibers formed of an at least partially metallic material;
   fibers formed of an at least partially synthetic polymeric material; and
   fibers formed of an at least partially natural material.

4. The conduit of claim 2, wherein the wall further comprises a flexible polymeric casing in contact with the reinforcement element.

5. The conduit of claim 2, wherein the fibers of the reinforcement element are of a woven configuration in a form of a cloth.

6. The conduit of claim 1, wherein the wall comprises a reinforcement element having fibers formed of the shape memory material.

7. The conduit of claim 1, wherein the flow element is further structured to be movable between the second configuration and a third configuration, the third configuration being a rolled configuration wherein at least a portion of a first outer surface of the first wall segment opposite the first inner surface and at least a portion of a second outer surface of the second wall segment opposite the second inner surface are engaged with one another.

8. The conduit of claim 7, wherein the flow element in the third configuration is structured to be rolled about an axis perpendicular to the direction of elongation.

9. An elongated flexible conduit structured to extend between a source of breathing gas and a patient interface, the conduit being structured to communicate a flow of breathing gas between the source of breathing gas and the patient interface to provide the flow of breathing gas to a patient, the conduit comprising:
   an elongated flow element, comprising a first elongated wall segment and a second elongated wall segment;
   the first wall segment being connected longitudinally with the second wall segment to form as the elongated flow element a wall that is continuous in a circumferential direction perpendicular to a direction of elongation;
   the flow element being structured to be movable between a first configuration and a second configuration;
   the first configuration being an expanded configuration wherein the wall is of a nominally annular cross sectional shape wherein at least a portion of a first inner surface of the first wall segment and at least a portion of a second inner surface of the second wall segment are opposed to one another and extend about a perimeter of an elongated interior region that is structured to carry the flow of breathing gas;
   the second configuration being a collapsed configuration wherein at least a portion of the first surface and at least a portion of the second inner surface are engaged with one another;
   the flow element being formed at least at least in part of a shape memory material which, in response to an application of an amount of heat to the flow element, is structured to return to a cold forged shape and to thereby return the wall from the collapsed configuration to the expanded configuration; and wherein the flow element is further structured to be movable between the second configuration and a third configuration, the third configuration being at least one of a rolled configuration and a folded configuration wherein at least a portion of a first outer surface of the first wall segment opposite the first inner surface and at least a portion of a second outer surface of the second wall segment opposite the second inner surface are engaged with one another, the flow element in the third configuration being structured to be at least one of rolled and folded about an axis parallel with the direction of elongation.

10. The conduit of claim 9, wherein the flow element in the third configuration is further structured to be longitudinally situated within an interior region of an elongated sheath.

11. The conduit of claim 9, in combination with an elongated sheath having an elongated interior region wherein the flow element in the third configuration is further structured to be longitudinally situated within the interior region of the elongated sheath.

* * * * *